United States Patent [19]

Kalopissis et al.

[11] 4,315,912
[45] Feb. 16, 1982

[54] CATIONIC SURFACTANTS

[75] Inventors: Gregoire Kalopissis, Neuilly-sur-Seine; Guy Vanlerberghe, Claye-Souilly; Henri Sebag, Paris, all of France

[73] Assignee: L'Oreal, Paris, France

[21] Appl. No.: 100,323

[22] Filed: Dec. 5, 1979

[30] Foreign Application Priority Data

Dec. 6, 1978 [FR] France .............................. 78 34418

[51] Int. Cl.$^3$ ...................... A61K 7/06; A61K 7/00; A61K 31/00; A61K 47/00
[52] U.S. Cl. ............................................ 424/70; 8/405; 424/47; 424/71; 424/168; 424/307
[58] Field of Search ............................ 424/47, 70, 307

[56] References Cited

U.S. PATENT DOCUMENTS 3,879,464  4/1975  Kalopissis et al. ................. 424/70 X

FOREIGN PATENT DOCUMENTS 1538525  9/1968  France .

Primary Examiner—Frank Cacciapaglia, Jr.
Attorney, Agent, or Firm—Cushman, Darby & Cushman

[57] ABSTRACT

A cationic surfactant of the formula

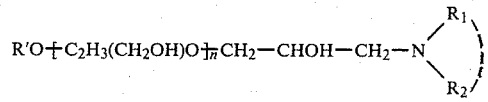

wherein R' represents a hydrocarbon radical containing up to 30 carbon atoms and derived from lanolin, natural waxes or resin acids, n is a number between 0.5 and 10, and $R_1$ and $R_2$ each independently represent lower alkyl or lower hydroxyalkyl, or together form a heterocycle such as morpholinyl or piperidinyl, is used to prepare cosmetic compositions for application to the skin or hair. Preferably, R' in the surfactant is derived from the alcohols of lanolin and hydrogenated lanolin.

12 Claims, No Drawings

CATIONIC SURFACTANTS

The present invention relates to cationic surfactants which are polyhydroxylated tertiary amines, the mineral or organic acid salts thereof or the quaternary ammonium salts thereof.

BACKGROUND OF THE INVENTION

In French Pat. No. 1,538,525 of July 25, 1967, which corresponds, essentially, to U.S. Pat. No. 3,879,464, there is described a process for preparing cationic surfactants of the formula

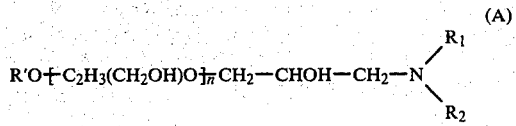
(A)

wherein

R represents linear or branched alkyl or alkenyl each having 8-22 carbon atoms or alkyl aryl wherein the alkyl moiety, linear or branched, contains from 8-22 carbon atoms, $R_1$ and $R_2$ each independently represent lower alkyl or lower hydroxyalkyl or together with the nitrogen atom to which they are attached form a heterocycle, and n is a number between 0.5 and 10 inclusive; as well as their quaternary derivatives of the formula:

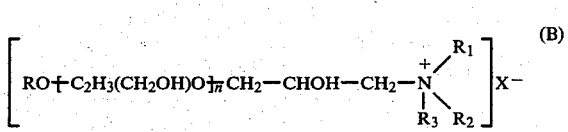
(B)

wherein

R, $R_1$, $R_2$ and n have the meanings given above, $R_3$ represents lower alkyl having 1-2 carbon atoms, and X represents an anion such as Cl, Br, I, $SO_4CH_3$ and $SO_4C_2H_5$.

These cationic surfactants of formulas (A) and (B) can be used in cosmetic compositions for the hair. However, it has been observed that they are not appropriate for the preparation of cosmetic compositions for the skin.

It has now been found that, by replacing in formulas (A) and (B) above, the substituent R which is there defined as an alkyl or alkenyl or alkyl aryl having from 8-22 carbon atoms, by a higher hydrocarbon radical derived from aliphatic and/or alicyclic and/or sterols of high molecular weight and more particularly derived from lanolin, from natural waxes and from resin acids, surfactants are obtained which do not exhibit this disadvantage and which can advantageously be used in cosmetic compositions for the skin.

GENERAL DESCRIPTION OF THE INVENTION

The present invention relates to new cationic surfactants of the formula:

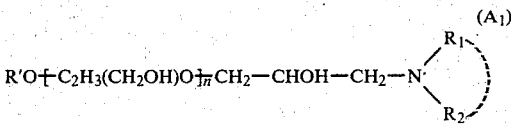
(A₁)

wherein

R' represents a hydrocarbon radical derived from aliphatic and/or alicyclic alcohols of high molecular weight and/or from sterols, of natural or synthetic origin, having up to 30 carbon atoms. Advantageously, R' is a hydrocarbon radical derived from alcohols and/or sterols obtained from lanolin, from natural waxes such as bees wax or from resin acids and is, more preferably, a hydrocarbon radical derived from the alcohols of lanolin or of hydrogenated lanolin;

n is a number between 0.5 and 10; and $R_1$ and $R_2$ represent lower alkyl or lower hydroxyalkyl radical, or $R_1$ and $R_2$ together with the nitrogen atom to which they are attached form a heterocycle having 5-6 chains and preferably a piperidinyl or morpholinyl radical.

The lower alkyl and hydroxy alkyl radicals have preferably from 1-4 carbon atoms.

The present invention also relates to the salts of the compounds of formula $A_1$ with mineral or organic acids, notably with hydrochloric acid, phosphoric acid, acetic acid, citric acid, lactic acid, tartaric acid and glycolic acid.

The present invention also relates to quaternary ammonium salts of the formula:

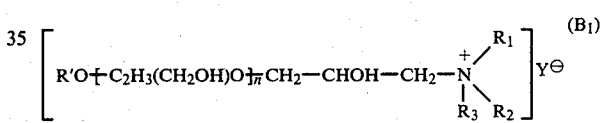
(B₁)

wherein

R', $R_1$ and $R_2$ have the meanings given above in ($A_1$), $R_3$ represents lower alkyl having 1-2 carbon atoms and Y⁻ represents an anion such as Cl, Br, I, $CH_3SO_4$ and $C_2H_5SO_4$.

It is known that the alcohols of lanolin, for example, have up to 30 carbon atoms and that they comprise a mixture of alcohols of the aliphatic series having a straight or branched chain and of alcohols of the alicyclic series (sterols and triterpenic alcohols). On saponification and extraction the alcohols which occur in lanolin are recovered essentially in the form of fatty acid esters. On hydrogenation a mixture comprising both the alcohols of the unsaponifiables and those which come from the fatty acids of lanolin are obtained.

In a similar fashion alcohols of high molecular weight can be obtained starting with natural waxes, such as beeswax, as well as resin acids.

The present invention also relates to a process for preparing cationic surfactants of formula ($A_1$) above, by the polyaddition on alcohols of the formula R'OH (R' having the meaning given above) of (n+1) moles of glycerol epihalohydrin of the formula:

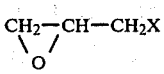

wherein

X represents a halogen atom, and preferably chlorine or bromine. The polyhalogenated polyether is then converted to polyhalogenated glycidyl ether by dehydrohalogenation of the halohydrin using an aqueous solution of an alkali metal or alkaline earth metal hydroxide. The resulting polyhalogenated glycidyl ether is then reacted with a secondary amine to form a polyhalogenated tertiary amine. The halogen of the polyhalogenated tertiary amine is then replaced by a hydroxyl group using an alkaline salt of a carboxylic acid in the presence or absence of an appropriate solvent. Optionally, the resulting polyhydroxylated tertiary amines can be quaternized using an appropriate quaternization agent.

The quaternization reaction provides the quaternary ammonium salts of formula ($B_1$) above.

The various stages of the process for preparing compound ($A_1$) as set forth above can schematically be represented as follows:

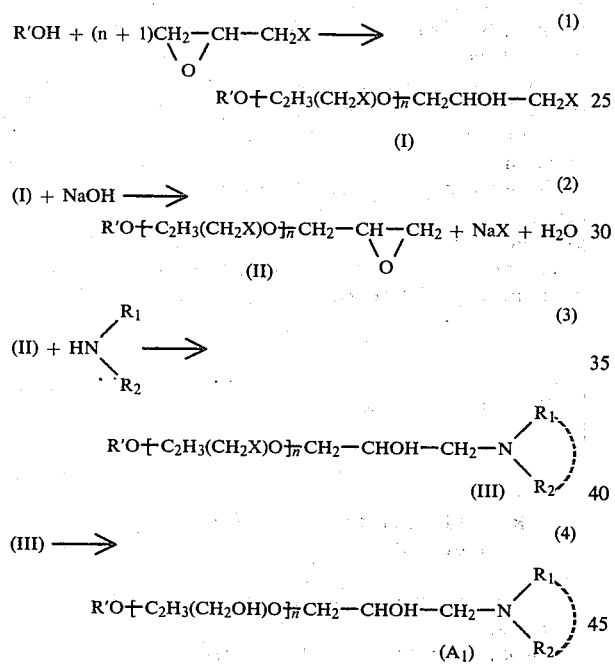

It is clear that during the polyaddition reaction which forms the first stage of the process of the present invention, a mixture of compounds, all corresponding to general formula (I) is formed but in which the number of moles of glycerol epihalohydrin fixed can be greater or smaller than the average statistical value corresponding to the number of moles of glycerol epihalohydrin used per mole of fatty alcohol.

It results from it that a mixture of compounds is obtained in which the aggregate of n values is statistically distributed around an average value corresponding to the number of moles of glycerol epihalohydrin used per mole of alcohol.

An important fact which should be emphasized and which corresponds to one of the essential advantages of the process of the present invention, is that the present process results in the formation of compounds having a single lipophilic chain per hydrophilic chain.

Moreover, the process of the present invention permits the regulation at will of the hydrophilic and lipophilic character of the final product. In effect, the hydrophilic character of the resulting compound can be regulated by choosing the value of the number n of moles of glycerol epihalohydrin to be reacted with one mole of fatty alcohol. The lipophilic characteristic of these final compounds can be regulated by selecting the length of the hydrocarbon chain R' in the fatty alcohol or sterol used as an initial reactant.

The following is a preferred embodiment of producing the surfactant of the present invention.

In a first stage (i), the polyaddition of glycerol epihalohydrin on the fatty alcohol is carried out in the presence of an acid catalyst such as boron trifluoride, stannic chloride or antimony pentachloride, at a temperature between 25°–160° C. Preferably, boron trifluoride is employed at a temperature between 50°–120° C. The proportion of $BF_3$ relative to the total weight of reactants ranges between 0.1 and 0.2 weight percent.

In the second stage (ii), the polyhalogenated polyethers of the formula:

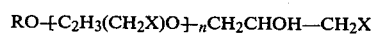

are then converted to glycidyl ethers by dehydrohalogenation of the halohydrin, using an aqueous solution of an alkali metal or alkaline earth metal hydroxide, having a concentration, by weight, in the order of 20–50%. The molar ratio of alkali-metal hydroxide or alkaline earth metal hydroxide to halohydrin is between 1:1 and 1:2, and preferably between about 1:1.2 to 1:1.5. The temperature during this reaction rises from an initial 20° C. to about 100° C. Generally, the reaction is initiated at ambient temperature, then when it is no longer exothermic, the reaction is terminated by heating the reaction mixture in a water bath.

In order to obtain the high reaction speeds and high epoxidation yields, a solvent is employed. It is quite advantageous to select a solvent which is non-miscible with concentrated aqueous solutions of electrolytes so that the resulting polyhalogenated glycidyl ethers can be separated from the reaction medium simply by decantation.

Tertiary butyl alcohol and 2-butoxy ethanol are particularly useful solvents when used in weight proportions essentially equal to that of the halohydrin to be dehydrohalogenated. In order to improve contact between the reactants, quaternary ammonium salts having a lipophilic chain can be used.

The resulting polyhalogenated glycidyl ether can be isolated by evaporation of the solvent or it can be used in solution in the course of the following stage of the preparation.

In a third stage (iii), the opening of the epoxide ring by a secondary amine is carried out at a temperature between 25° and 120° C.

Alternatively, in a single operation the polyhalogenated tertiary amine can be obtained by reacting directly the halohydrin with a secondary amine in the presence of an alkali metal hydroxide or alkaline earth metal hydroxide.

The secondary amines usefully employed in the present invention include diethylamine, dipropylamine, morpholine, piperidine, as well as alkanolamines such as diethanolamine, diisopropanolamine, diglycerylamine and N-ethylethanolamine.

In an advantageous embodiment of the present invention, the polyhalogenated polyether is reacted with a secondary amine in the presence of an alkali metal hydroxide or alkaline earth metal hydroxide without isolating the glycidyl ethers resulting therefrom. After reaction with an alkaline salt of carboxylic acid, the esterified amino polyethers are separated from the mineral halide by filtration or washing, and the salts of the carboxylic acid are regenerated in situ from the carboxylic esters by saponification with an alkali metal hydroxide or alkaline earth metal hydroxide. Thus the alkali or alkaline earth salt of the carboxylic acid is recovered in aqueous solution and can be reused for another hydroxylation reaction.

The molar proportions of secondary amine to epoxide (when the glycidyl ether of formula II is isolated) or the molar proportions of secondary amine to halohydrin (when the secondary amine is reacted directly without isolating the glycidyl ethers of formula II) are between 1:1 and about 1:1.5. The preferred proportions is of the order 1:1.2.

In a fourth stage (iv), the replacement of the halogen by a hydroxy yields the polyhydroxylated amines of the present invention, having the formula

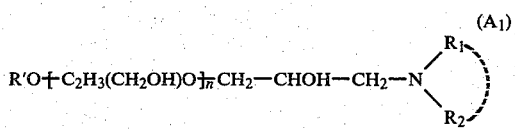
(A₁)

This operation is carried out with an alkaline salt of a carboxylic acid such as sodium or potassium acetate, at a temperature between 150°–200° C., and preferably close to 180° C., in the presence or absence of a solvent.

The presence of a solvent in the reaction medium during step (iv) assures both instantaneous and progressive contact among the reactants and easy separation therefrom of the mineral halide formed. Suitable solvents include ethylene glycol, diethylene glycol, propylene glycol, dipropylene glycol, as well as the monoalkylethers of these diols, such as the monobutyl ether of ethylene glycol and the monobutyl ether of diethylene glycol. The hydroxylated solvents also intervene by alcoholysis of the esters formed in an intermediate stage.

When the reaction is carried out in the absence of a solvent, as may be the case when the alkaline salt of the carboxylic acid exhibits a certain solubility in the reaction medium, the polyhydroxylated tertiary amine is obtained by alcoholysis of the esters of the carboxylic acid with a lower alcohol such as methanol or ethanol or by saponification followed by salting out or extraction.

In a fifth stage (v), the polhydroxylated tertiary amines of the general formula

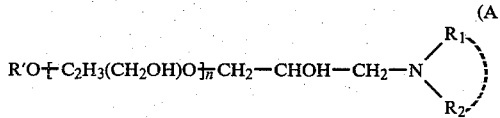
(A₁)

can be converted to salts of a mineral or organic acid, or converted to quaternary ammonium salts of the formula:

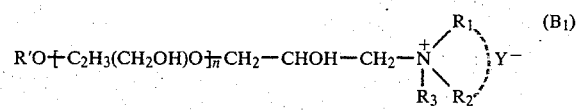
(B₁)

wherein

R', R₁, R₂ and n have the meanings given above,

R₃ represents a lower alkyl radical having 1–2 carbon atoms, and

Y⁻ represents an anion such as Cl, Br, I, CH₃SO₄ and C₂H₅SO₄.

In particular, the use of methylsulfate easily provides quaternary ammonium compounds by an alkylation reaction carried out at a temperature lower than 100°–110° C.

The compounds of formula (A₁) as well as their acid salts, and the quaternary ammonium salts (B₁), are very important surfactants.

These products can also be used in the form of salts of mineral acids such as hydrochloric acid, phosphoric acid and boric acid or organic acids such as acetic acid, citric aid, lactic acid and tartaric acid.

The present invention also relates to a new industrial product comprising the new cationic surfactants of formula (A₁) or their quaternary ammonium salts (B₁) obtained by the above mentioned process.

By varying the radicals R₁, R₂ and n, it is possible to obtain a very large range of products.

Compared, for example, with fatty amines, the surfactants of the present invention have the following advantages:

(a) The are significantly more water soluble and especially at a pH close to neutrality, and (b) They are essentially free of the characteristic odor of fatty amines and derivatives thereof.

Moreover, the process of the present invention yields stable surfactants which are soluble in water over a wide pH range. In particular, the present invention provides surfactants which are soluble in concentrated NaOH solutions without risk of instability which occurs, for example, with quaternary ammonium hydroxides. Moreover, this result is obtained without the introduction of supplementary ionic groups and especially anionic which impair the substantive characteristics of the surfactants. The solubility characteristics of the surfactants of this invention are, of course, highly variable as a function of the values of n, R', R₁ and R₂.

The surfactants of this invention are clearly less aggressive than fatty amines and derivatives thereof and they also compare very advantageously to aminated polyethers of the formula:

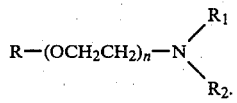

The substitution of a [C₂H₃O(CH₂OH)] group for an oxyethylene group (C₂H₄O) is very advantageous in terms of its water-solubility characteristics.

The cationic surfactants of formula (A₁) and their quaternary ammonium salts of formula (B₁) are distinguished from compounds of formulas (A) and (B) of the prior art by their greater emulsifying properties.

This advantageous characteristic results in the provision of cosmetic preparations which have a greater affinity vis-a-vis the skin and in which treating agents such as bactericides, in particular, quaternary ammonium salts and antiseborrheic agents can be introduced.

The use of the cationic emulsifying agents of formulas $A_1$ and $B_1$ in cosmetology and in dermatology is advantageous for they permit the preparation of cosmetic compositions having a slightly alkaline or even acid reaction (pH 5 to 8) which is useful in the care and treatment of the skin.

The use of known cationic surfactants has until now been discouraged for several reasons, principally because of (a) their toxicity and aggressivity, (b) their incompatibility with other components of cosmetic formulations. The flocculating properties of quaternary ammonium salts are well known, and (c) their significant water-solubility characteristics leads to poor emulsifying properties.

The surfactants of formulas $A_1$ and $B_1$ do not exhibit these disadvantages.

Moreover, it is well known, depending on the nature of the oil to be emulsified, the hydrophile-lipophile balance (H.L.B.) of the emulsifying agent must be more or less accentuated. The process of preparing the compounds of the present invention responds particularly well to this exigency. Thus, depending on the choice of the values of n and the nature of the $R_1$ and $R_2$ substituents, the H.L.B. of the surfactant of the present invention can be modified within wide limits. Further, the H.L.B. of the surfactant of this invention can also be modified by salifying the surfactant or by a total or partial quaternization thereof.

The present invention also relates to a new cosmetic composition and, particularly, one for use in the care and treatment of the hair and skin. The cosmetic composition of this invention contains at least one surfactant of formula $(A_1)$, optionally in the form of an acid salt, or a quaternary ammonium salt of formula $(B_1)$.

Representative cosmetic compositions include shampoos, before- and after-shampoo treating lotions, hair setting lotions, permanent wave lotions, hair rinses, hair dyes, fixatives for permanent waves, hair brushing lotions, eye make-up remover lotions, protective milks and creams for the face, make-up remover milks and creams, anti-acne milks and creams, milks, creams and gels for softening the hands, hydrating milks and creams, body milks and creams, foaming creams, make-up bases, anti-solar compositions, antiperspirant creams and deodorant creams.

These compositions can be provided in the form of an aqueous or hydroalcoholic solution, a cream, a gel, an oil-in-water emulsion, a suspension, an aqueous or hydroalcoholic dispersion, a compact product or packaged in the form of an aerosol.

Additionally, the cosmetic composition of the present invention can also include, in addition to one or more cationic surfactants of formula $(A_1)$ or $(B_1)$, one or more of another cationic surfactant, an amphoteric surfactant, nonionic surfactant, a hair dye, a perfume, a preservative, a sequestering agent, a thickener, a softening agent, a humectant, an agent for protection against UV radiations, a fatty body, an animal, mineral, vegetable or synthetic oil or wax, a fatty ester, a fatty alcohol, a cationic, nonionic or amphoteric resin or polymer, a natural gum or resin optionally modified, an emulsifying agent, a solar filter, an organic solvent, an opacifier, an antioxidant, a nacreous lusterant, a pH modifying agent, a reducing agent, an electrolyte, an oxidant, a natural substance, a protein derivative, an antiseborrheic agent, an antipellicular agent, a hair restructuring agent, an active substance capable of having an activity at the treatment level of the skin or the protection of the skin or hair, a solvent such as a lower alcohol having 1–4 carbon atoms, a glycol and a glycol ether.

The cosmetic composition of the present invention includes generally from 0.1–30% of the surfactant of formula $(A_1)$ and/or $(B_1)$. The pH of this composition is generally between 3 and 10.

The cationic surfactant of formulas $(A_1)$ and $(B_1)$ when used for the treatment of the hair, imparts thereto a shiny aspect and a more agreeable feel or touch. The hair thus treated is particularly soft, odorless and combs easily.

The cationic surfactant of formulas $(A_1)$ and $(B_1)$ are quite useful in the preparation of stable emulsions for the care of the skin without the need of any other emulsifying agent.

The cosmetic composition for the care and treatment of the skin in accordance with the present invention is preferably provided in the form of an oil-in-water emulsion, an aqueous or hydroethanolic solution or a gel.

The oil-in-water emulsions includes 0.1–30% by weight of one or more surfactants of formulas $(A_1)$ or $(B_1)$; from 5 to 60% by weight of a fatty body or a synthetic, mineral, animal or vegetable oil or wax, and from 10–95% by weight water.

However, the cationic surfactants of formula $(A_1)$ and the acid salts thereof are preferably employed as emulsifying agents in cosmetic compositions for the skin as opposed to the surfactants of formula $(B_1)$. These latter, which are more hydrophilic, are more appropriate for use in capillary preparations such as shampoos, permanent wave lotions, hair dye vehicles, hair rinsing lotions and hair conditioning lotions.

All the compositions for the care of the skin can also include one or more adjuvants selected from polymers and preferably among the cationic polymers; surfactants and preferably cationic surfactants; animal, vegetable, mineral or synthetic oils and waxes; humectants; UV radiation protective agents; antiseborrheic agents; antioxidants; natural gums and resins optionally modified; protein derivatives; natural substances having an activity for the treatment or care of the skin; pH modifying agents; and solvents such as ethanol.

The present invention also relates to a process for the treatment of the hair or skin comprising applying to the hair or skin an effective amount of the above-described cosmetic composition.

The following non-limiting examples are given to illustrate the invention. Unless otherwise specified, all parts and percentages are by weight.

EXAMPLES OF PREPARATION

Example I.

Preparation of a mixture of compounds of the formula

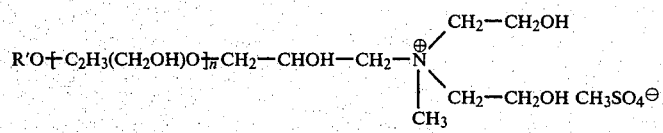

wherein R' represents the residue of lanolin alcohols and n represents a statistical average value of 1.

To 300 g (720 meq) of lanolin alcohols, sold by Crod under the commercial name "Satulan", there are added 1.73 ml of the etherate of BF$_3$, then 133.2 g (1.44 moles) of epichlorohydrin at 50°–55° C. are added over a period of 1 hour 30 minutes. The reaction medium is then left for about 30 minutes with agitation at the same temperature.

There is thus obtained a polyhalogenated derivative in the form of a pasty, light brown colored product whose hydroxyl index is 1.57 meq/g.

To 140 g of the polyhalogenated derivative thus obtained, there are added, in the space of 20 minutes, 25 g of 40% NaOH, at a temperature of 45° C. After 1 hour of agitation at this temperature, 140 g of tertiary butyl alcohol are added. Then, in the space of 10 minutes, 26.3 g (233 meq) of diethanolamine are added. The reaction medium is then left under agitation at the reflux temperature of the alcohol for 2 hours 30 minutes.

The reaction mass is taken up in 50 g of water and after 30 minutes under agitation at 80° C., the aqueous phase is separated by decanting.

The remaining organic phase is washed twice with 150 ml of boiling water and then dehydrated by heating under reduced pressure.

To 132 g (200 meq in chloride) of the resulting product 132 g of dipropylene glycol and 20.6 g (210 meq) of potassium acetate are added. The reaction mass is then heated with agitation and under a nitrogen atmosphere, at 180° C. for 6 hours. Thereafter, the reaction mass is washed twice with 400 ml of boiling water. The organic phase is then saponified by the addition of 21.2 g of NaOH (at 9.9 meq/g) in the presence of 70 ml of isopropanol and heated at the reflux temperature for 1 hour.

The reaction medium is washed with water in the presence of hydrochloric acid.

To 40 g (56.8 meq) of the cationic derivative prepared immediately above, there are added 13 g of methanol. Then 7.11 g (56.4 meq) of dimethyl sulfate are added over a period of 1 hour at 35° C. The reaction medium is then left with agitation for 1 hour 30 minutes at this temperature.

After removal of the methanol, a product provided in the form of a soft, brown colored paste, soluble in water with a slight opalescence is obtained.

Example II.

Preparation of a mixture of compounds of the formula

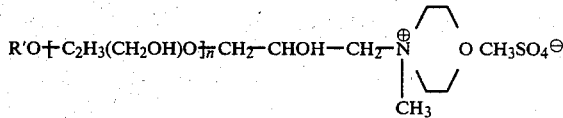

wherein R' represents the residue of lanolin alcohols and n has a statistical average value of 1.

To 278.5 g (442 meq in hydroxyl groups) of the polyhalogenated derivative obtained in Example I, there are added 278 g of tertiary butyl alcohol. Then, at 45° C., 70.23 g of NaOH (9.9 meq/g) are added over a 10-minute period. The reaction medium is heated with agitation at 50°–60° C. for 30 minutes. The resulting product is then washed twice with 600 ml of water at 70° C. After dehydration under reduced pressure, a light brown paste whose epoxide index is 2 meq/g is obtained.

To 60 g (120 meq) of the derivative prepared immediately above, there are added in a 30-minute period at 80° C. and under a nitrogen atmosphere, 11.5 g (142 meq) of morpholine. After 3 hours of agitation at 80°–85° C., the resulting product is washed three times with 100 ml of boiling water. The product is then dehydrated by heating under reduced pressure.

A light brown paste whose basic index is 1.39 meq/g, and whose chloride index is 1.58 meq/g is obtained.

To 58 g (86.63 meq in chloride) of the preceding product, there are added 58 g of dipropylene glycol and 8.8 g (91 meq) potassium acetate. The reaction medium is then heated with agitation and under a nitrogen atmosphere, at 180° C. for 6 hours.

The product obtained is washed three times with 100 ml of boiling water in the presence, optionally, of isopropanol to facilitate its salting out. It is then saponified with 9.2 g of NaOH (9.9 meq/g) at 80° C. for 1 hour 30 minutes.

The reaction mass is washed three times with 100 ml of boiling water and then dried by heating under reduced pressure.

A brown paste soluble in water in the presence of an acid and whose basic index is 1.43 meq/g is obtained.

To 45 g (65 meq in basicity) of the product obtained immediately above, there are added 10 g of methanol. Then at 35° C., in the space of one hour, 8.1 g of dimethyl sulfate are added. The heating and agitation of the reaction medium is maintained for an additional hour. A brown paste soluble in water after heating is obtained.

Example III.

Preparation of a mixture of compounds of the formula $$R'O+C_2H_3(CH_2OH)O\}_{\overline{n}}CH_2-CHOH-CH_2-\overset{+}{N}\underset{CH_3}{\overset{\diagup CH_2CH_2OH}{\diagdown CH_2CH_2OH}} \quad CH_3SO_4^{\ominus}$$

wherein R' is the residue of lanolin alcohols and n represents a statistical average value of 2.

To 300 g (720 meq) of lanolin alcohols, sold under the trade name "Satulan", there are added 2 ml of the etherate of BF₃. Then at 50°–55° C. in the space of one hour 30 minutes, there are added 199.8 g (2.16 moles) of epichlorohydrin. The reaction mixture is then left for 1 hour 30 minutes under agitation at the same temperature.

To 482 g (694 meq) of the polyhalogenated derivative obtained immediately above, there are added 480 g of tertiary butyl alcohol. Then, in a period of 10 minutes, at a temperature of 50° C., 129.6 g of NaOH (9.9 meq/g) are added. The reaction mixture is then left under agitation for 30 minutes at 60° C. and under a nitrogen atmosphere.

The product is washed 3 times with 900 ml of water at 60°–70° C. and then dehydrated under reduced pressure.

A light brown paste whose epoxide index is 1.48 meq/g is obtained.

To 120 g (177.6 meq in epoxide groups) of the derivative prepared immediately above, there are added in a 15-minute period at 80° C. and under the nitrogen atmosphere, 25.5 g (237 meq) of diethanolamine. After two hours of agitation at this temperature, the product is washed three times with 200 ml of boiling water, in the presence, optionally, of chloroform to facilitate its decanting. The product is then dried by heating under reduced pressure.

A pasty product whose basic index is 1.19 meq/g is obtained.

To 127 g (332 meq in chloride) of the preceding product, there are added 127 g of dipropylene glycol and 34.1 g of potassium acetate. The reaction medium is then heated under agitation and a nitrogen atmosphere at 180° C. for 6 hours. The product obtained is then washed 3 times with 200 ml of water in the presence, optionally, of butanol to facilitate its decanting. The product is then saponified with 34.5 g of NaOH (9.9 meq/g) at 90° C. for 1 hour 15 minutes. The reaction mass is washed three times with 260 ml of boiling water and then dehydrated by heating under reduced pressure.

The product thus obtained has a basic index of 1.33 meq/g.

To 30 g (40 meq in basicity) of the product obtained immediately above, there are added 5 g (0.04 mole) of dimethyl sulfate at 30°–35° C. in one hour. The reaction mixture is left for one hour under agitation at this temperature.

A light brown paste which exhibits a slight cloud in water is obtained.

Example IV.

Preparation of a mixture of compounds of the general formula:

$$R'O+C_2H_3(CH_2OH)O\}_{\overline{n}}CH_2-CHOH-CH_2-N\underset{C_2H_5}{\overset{\diagup C_2H_5}{\diagdown}}$$

wherein R' is the residue of lanolin alcohols and n represents a statistical average value of 6.

To 100 g (240 meq) of lanolin alcohols there are added 1.02 ml of the etherate of BF₃. Then 155.4 ml (1680 meq) of epichlorohydrin are added at 50°–55° C., in a three-hour period, under a nitrogen atmosphere. The reaction mixture is left for 30 minutes under agitation at the same temperature.

To 248 g (233.4 meq) of the polyhalogenated derivative obtained immediately above, there are added 240 g of tertiary butyl alcohol. Then, at 50° C., 45.4 g of NaOH (9.9 meq/g) are added in a 10-minute period. The reaction mixture is left under agitation for one hour at 60° C.

The product is washed twice with 300 ml of hot water and then dehydrated under reduced pressure. It is provided in the form of a very light brown colored paste whose epoxide index is 1.07 meq/g.

To 100 g (107 meq) of the preceding derivative, then are added under a nitrogen atmosphere, at 65°–70° C., 16.5 g of diethylamine in a 15-minute period. The reaction mixture is then left under agitation at 60° C. for three hours.

The product is washed with 400 ml of hot water and then dehydrated by heating under reduced pressure.

To 90 g (491 meq in chloride) of the immediately preceding product, there are added 90 g of dipropylene glycol and 50.6 g of potassium acetate. The reaction mixture is heated, under agitation and a nitrogen atmosphere, to 180° C. for six hours. The product obtained is washed twice with 150 ml of hot water and then dehydrated by heating under reduced pressure.

80 ml of absolute methanol and 0.8 g of sodium methylate at 5.4 meq/g are added.

After standing overnight at ambient temperature, the solvent is removed by heating under reduced pressure.

A brown paste soluble in water with a slight cloud which disappears on the addition of a mineral or organic acid and whose basic index is 0.87 meq/g is thus obtained.

Example V

Preparation of a mixture of compounds of the formula $$R'O+C_2H_3(CH_2OH)O\}_{\overline{n}}CH_2-CHOH-CH_2-N\underset{CH_2-CH_2OH}{\overset{\diagup CH_2-CH_2OH}{\diagdown}}$$

wherein R' is the residue of lanolin alcohols and n has a statistical average value of 2.

To 300 g of lanolin alcohols (0.72 equivalents in hydroxyl groups) there are added 2 ml of the etherate of BF$_3$. Then 200 g (2.16 moles) of epichlorohydrin are added at 50°–55° C., over a period of 1 hour 30 minutes, under a nitrogen atmosphere. The reaction mixture is left for 1 hour 30 minutes under agitation at the same temperature.

To 482 g (0.69 mole) of the polyhalogenated derivative obtained immediately above, there are added 480 g of tertiary butyl alcohol. Then at 50° C., 105 g of NaOH (9.9 meq/g) are added in a 10-minute period. The reaction mixture is left under agitation for 1 hour at 60° C.

The product is washed twice with 300 ml of hot water and then dehydrated under reduced pressure. It is provided in the form of a very light brown colored paste whose epoxide index is 1.48 meq/g.

To 120 g (183 meq, in epoxide groups) of the preceding derivative, there are added, under a nitrogen atmosphere, at 65°–70° C., 25.6 g (0.23 mole) of diethanolamine in 15 minutes. The reaction mixture is left under agitation at 80° C. for 2 hours.

The product is washed three times with 200 ml of hot water and then dehydrated by heating under reduced pressure.

To 127 g (332 meq in chloride) of the preceding product, there are added 127 g of dipropylene glycol and 34.1 g of potassium acetate. The reaction mixture is then heated under agitation and a nitrogen atmosphere at 180° C. for 6 hours. The product obtained is saponified at 90° C. with 34.5 g of NaOH (10 meq/g), washed three times with 200 ml of boiling water and then dehydrated by heating under reduced pressure.

The product thus obtained is provided in the form of a soft paste whose basic index is 1.33 meq/g.

EXAMPLES OF COSMETIC COMPOSITIONS AND USES THEREOF

Example 1

The following pre-shampoo lotion is prepared:
Cationic polymer of the formula:

$$\left[\begin{array}{c} CH_3 \\ \overset{\oplus}{N}-(CH_2)_3 \\ | \\ CH_3 \;\; Cl^{\ominus} \end{array} \begin{array}{c} CH_3 \\ \overset{\oplus}{N}-(CH_2)_6 \\ | \\ CH_3 \;\; Cl^{\ominus} \end{array}\right]_n (CT1)$$

| | |
|---|---|
| | 0.4 g (active material) |
| Compound of Example I | 0.5 g |
| Alkyl dimethyl hydroxyethyl ammonium chloride (alkyl derived from the fatty acid of tallow) | 0.7 g |

Cationic polymer of the formula:

$$\left[\begin{array}{c} CH_3 \\ \overset{\oplus}{N}-(CH_2)_3 \\ | \\ CH_3 \;\; Cl^{\ominus} \end{array} \begin{array}{c} CH_3 \\ \overset{\oplus}{N}-CH_2CONH(CH_2)_2-NHCOCH_2 \\ | \\ CH_3 \;\; Cl^{\ominus} \end{array}\right]_n (CT2)$$

| | |
|---|---|
| | 1 g |
| Citric acid, sufficient for pH = 7 | |
| Water, sufficient for | 100 g |

This solution is applied to dirty and previously moistened hair. After massaging the solution into the hair, the hair is rinsed with water. A conventional shampoo composition is then applied to the hair. After rinsing and drying, the hair thus treated is shiny and soft.

Example 2

The following pre-shampoo lotion is prepared:

| | |
|---|---|
| Compound of Example II | 1g |
| Cationic polymer (CT1), as in Example 1 | 0.6g |
| Cationic polymer of adipic acid/dimethylaminohydroxypropyl diethylene triamine, sold under the name "Cartaretine F.4" by Sandoz | 1g |
| Citric acid, sufficient for pH = 7 | |
| Water, sufficient for | 100g |

This solution is applied to dirty hair previously moistened. After massaging the solution into the hair, the hair is rinsed with water. A conventional shampoo composition is then applied to the hair. After rinsing and drying, the hair thus treated is shiny, soft and well controlled.

Example 3

The following pre-shampoo lotion is prepared:

| | |
|---|---|
| Compound of Example III | 1g |
| Cationic polymer, (CT1), as in Example 1 | 0.3g |
| Cationic polymer, (CT2), as in Example 1 | 1.5g |
| Citric acid, sufficient for pH = 7 | |
| Water, sufficient for | 100g |

This solution is applied to dirty hair previously moistened. After massaging the solution into the hair, the hair is rinsed with water. A conventional shampoo composition is then applied to the hair. After rinsing and drying, the hair thus treated is shiny, full and lively.

Example 4

The following after-shampoo composition is prepared:

| | |
|---|---|
| Cetylstearyl alcohol, partially oxyethylenated with 33 moles of ethylene oxide | 3g |
| Oleic alcohol | 1g |
| Compound of Example I | 4g |
| Hydroxyethyl cellulose, sold under the name "Cellosize WP 4400", by Union Carbide | 0.5g |
| Water, sufficient for | 100g |

The pH of this composition is 5.7.

This composition which is provided in the form of a fluid emulsion is applied to clean and moist hair. The composition is permitted to remain in contact with the hair for a few minutes. The hair is then rinsed. The hair thus treated is soft, full and shiny.

Example 5

The following after-shampoo composition is prepared:

| | |
|---|---|
| Cetylstearyl alcohol, partially oxyethylenated with 33 moles of ethylene oxide | 3g |
| Compound of Example II | 2.5g |
| Lactic acid, sufficient for pH = 3.5 | |
| Water, sufficient for | 100g |

This composition, which is provided in the form of a fluid emulsion, is applied to clean and moist hair. The composition is permitted to remain in contact with the hair for a few minutes. The hair is then rinsed. The wet hair combs easily; the hair when dried is soft, controlled and shiny.

Example 6

The following after-shampoo composition is prepared:

| | |
|---|---|
| Cetylstearyl alcohol, partially oxyethylenated with 33 moles of ethylene oxide | 3g |
| Oleic alcohol | 1g |
| Compound of Example III | 2.3g |
| Lactic acid, sufficient for pH = 3.5 | |
| Water, sufficient for | 100g |

This composition, which is provided in the form of a fluid emulsion, is applied to clean and moist hair. The composition is permitted to remain in contact with the hair for a few minutes. The hair is then rinsed. When dried, the hair is lively, shiny and full.

Example 7

The following shampoo composition is prepared:

| | |
|---|---|
| Triethanolamine lauryl sulfate | 12.5 g |
| Amphoteric surfactant of the formula 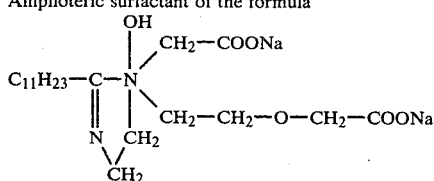 sold under the name "Miranol C2M" | 4 g |
| Diethanolamides of the fatty acids of copra | 3 g |
| Compound of Example I | 1.5 g |
| Water, sufficient for | 100 g |

The pH of this composition is 7.

This solution is applied to previously moistened hair. The solution is massaged into the hair so as to emulsify all the dirt. The hair is then thoroughly rinsed with water. A second application to the hair of the above solution is then effected. An abundant foam is obtained and the hair is then rinsed. The hair thus washed is soft, shiny and non-electric.

Example 8

The following shampoo is prepared:

| | |
|---|---|
| Sodium lauryl ether sulfate oxyethylenated with 2.2 moles of ethylene oxide | 10g |
| Alkyl ($C_{12}$—$C_{18}$) dimethyl carboxymethyl ammonium hydroxide, sold under the name "Dehyton AB30" by Henkel | 8g |
| Diethanolamides of the fatty acids of copra | 2g |
| Compound of Example II | 2g |
| Quaternized copolymer of vinyl pyrrolidone and another copolymerizable vinyl monomer having a molecular weight of about 1 million and sold under the name "Gafquat 755" by GAF | 0.5g |
| Water, sufficient for | 100g |

The pH is equal to 6.5.

This solution is applied to previously moistened hair. The solution is massaged into the hair so as to emulsify all the dirt. The hair is then rinsed thoroughly with water. A second application to the hair of this solution is then effected. An abundant foam is obtained and the hair is then rinsed. The hair thus washed is soft, shiny and non-electric.

Example 9

Protective cream for the face

| | |
|---|---|
| Petrolatum oil - Codex | 20g |
| Cetyl laurate, sold under the name "Cetiol LC" by Henkel | 15g |
| Compound of Example V | 8g |
| Quarternary copolymer of poly-vinylpyrrolidone having a molecular weight of about 1 million, sold under the name "Gafquat 755" by General Aniline | 0.3g |
| Preservative | 0.2g |
| Perfume | 0.3g |
| Sterile, demineralized water, sufficient for | 100g |

Example 10

Anti-acne cream

| | |
|---|---|
| Petrolatum oil - Codex | 15g |
| Isopropyl myristate | 5g |
| Carboxymethyl cysteine (anti-seborrheic agent) | 0.5g |
| Trimethyl cetyl ammonium bromide, sold under the name "Cetavlon" by I.C.I. | 0.2g |
| Compound of Example V | 5.6g |
| Perfume | 0.3g |
| Preservative | 0.3g |
| Sterile, demineralized water, sufficient for | 100g |

Example 11

Oil-in-water emulsion cream

| | |
|---|---|
| Cetyl laurate, oil sold under the name "Cetiol LC" by Henkel | 40g |
| Compound of Example V | 10g |
| Perfume | 0.3g |
| Preservative | 0.3g |
| Sterile, demineralized water, sufficient for | 100g |

Example 12

Eye make-up remover lotion

|  |  |
|---|---|
| Compound of Example IV | 3g |
| Lactic acid | 0.1g |
| Trimethyl cetylammonium bromide, sold under the name "Cetavlon" by I.C.I. | 0.1g |
| Perfume | 0.3g |
| Preservative | 0.3g |
| Sterile, demineralized water, sufficient for | 100g |

Example 13

Make-up remover lotion for oily skin

| | |
|---|---|
| Compound of Example II | 4 g |
| Ethyl alcohol | 4 g |
| Cationic surfactant of the formula: 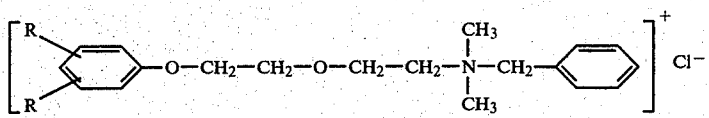 sold under the name, "Hyamine 1622", by Rhom & Haas | 0.1 g |
| | 0.1 g |
| Trans thiolane 3,4-diol S-dioxide (anti-seborrheic agent) | 0.3 g |
| Perfume | 0.5 g |
| Preservative | 0.4 g |
| Sterile, demineralized water, sufficient for | 100 g |

Example 14

Softening gel for the hands

|  |  |
|---|---|
| Compound of Example III | 4.5g |
| Quarternized guar gum, sold under the name "Guar HP 13" by Meyhall Chemicals | 0.4g |
| Quarternary derivative of cellulose ethers, sold under the name "JR 400" by Union Carbide | 0.5g |
| Perfume | 0.3g |
| Preservative | 0.3g |
| Demineralized water, sufficient for | 100g |

What is claimed is:

1. A cosmetic composition for the treatment of the hair or skin comprising at least one cationic surfactant of the formula

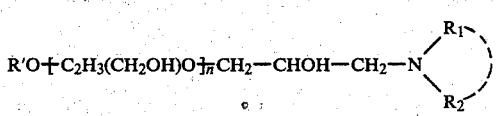

wherein
R' represents a hydrocarbon radical derived from a member selected from the group consisting of alcohols and sterols of a member selected from the group consisting of lanolin and hydrogenated lanolin,
n is a number between 0.5 and 10, and
$R_1$ and $R_2$ are selected from the group consisting of lower alkyl containing 1–4 carbon atoms and lower hydroxyalkyl wherein the alkyl moiety contains 1–4 carbon atoms, or $R_1$ and $R_2$ together with the nitrogen atom to which they are attached form a heterocycle containing 5 or 6 chains.

2. The cosmetic composition of claim 1 wherein $R_1$ and $R_2$ together form a heterocycle selected from the group consisting of piperidine and morpholine.

3. The cosmetic composition of claim 1 wherein said cationic surfactant is in the form of a salt of a mineral or organic acid.

4. In a cosmetic composition for the skin the improvement comprising as an emulsifying agent therefor a cationic surfactant of claim 1 or an acid salt thereof.

5. A cosmetic composition for the treatment of the hair or skin comprising at least one quaternary ammonium salt of the formula

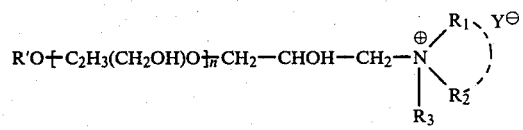

wherein
R' represents a hydrocarbon radical derived from a member selected from the group consisting of alcohols and sterols of a member selected from the group consisting of lanolin and hydrogenated lanolin,
n is a number between 0.5 and 10,
$R_1$ and $R_2$ are selected from the group consisting of lower alkyl containing 1–4 carbon atoms and lower hydroxyalkyl wherein the alkyl moiety contains 1–4 carbon atoms, or $R_1$ and $R_2$ together with the nitrogen atom to which they are attached form a heterocycle containing 5 or 6 chains,
$R_3$ represents lower alkyl having 1–2 carbon atoms, and
Y represents a member selected from the group consisting of Cl, Br, I, $CH_3SO_4$ and $C_2H_5SO_4$.

6. The cosmetic composition of claim 5 wherein $R_1$ and $R_2$ together form a heterocycle selected from the group consisting of piperidine and morpholine.

7. In a cosmetic composition for the hair including a shampoo, a pre-shampoo composition and an after-shampoo composition the improvement comprising an effective amount of the cationic surfactant of claim 5.

8. A composition for the care and treatment of the skin comprising 0.1–30 percent by weight of at least one cationic surfactant of claims 1 or 5 in the form of an oil-in-water emulsion, an aqueous or hydroalcoholic solution or a gel.

9. A composition for the care and treatment of the skin comprising an oil-in-water emulsion containing 0.1–30 weight percent of at least one cationic surfactant of claims 1 or 5, 5-60 weight percent of a fatty body or an animal, vegetable, mineral or synthetic oil or wax, and 10-95 weight percent water.

10. A process for treating the hair or skin comprising applying thereto an effective amount of the cosmetic composition of claims 1 or 5.

11. A cosmetic composition for the care of the hair or skin comprising an aqueous or hydroalcoholic solution of a cationic surfactant selected from the group consisting of
(1) a surfactant of the formula

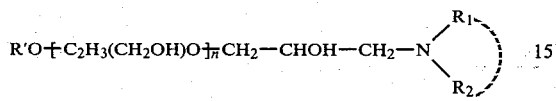

wherein
R' represents a hydrocarbon radical derived from a member selected from the group consisting of alcohols and sterols of a member selected from the group consisting of lanolin and hydrogenated lanolin,
n is a number between 0.5 and 10, and
$R_1$ and $R_2$ are selected from the group consisting of lower alkyl containing 1-4 carbon atoms and lower hydroxyalkyl wherein the alkyl moiety contains 1-4 carbon atoms, or $R_1$ and $R_2$ together with the nitrogen atom to which they are attached form a heterocycle containing 5 or 6 chains, and
(2) a surfactant of the formula

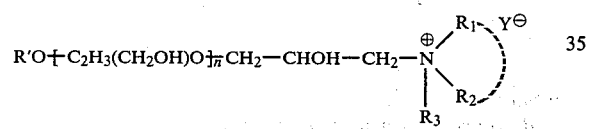

wherein
R' represents a hydrocarbon radical derived from a member selected from the group consisting of alcohols and sterols of a member selected from the group consisting of lanolin and hydrogenated lanolin,
n is a number between 0.5 and 10,
$R_1$ and $R_2$ are selected from the group consisting of lower alkyl containing 1-4 carbon atoms and lower hydroxyalkyl wherein the alkyl moiety contains 1-4 carbon atoms, or $R_1$ and $R_2$ together with the nitrogen atom to which they are attached form a heterocycle containing 5 or 6 chains,
$R_3$ represents lower alkyl having 1-2 carbon atoms, and
Y represents a member selected from the group consisting of Cl, Br, I, $CH_3SO_4$ and $C_2H_5SO_4$, said cationic surfactant being present in an amount of 0.1 to 30 percent by weight of said composition, said composition having a pH between 3 and 10.

12. A cosmetic composition for the skin in the form of an oil-in-water emulsion comprising
(a) 0.1-30 percent by weight of a cationic surfactant selected from the group consisting of
(1) a surfactant of the formula

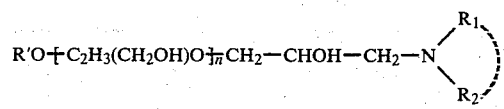

wherein
R' represents a hydrocarbon radical derived from a member selected from the group consisting of alcohols and sterols of a member selected from the group consisting of lanolin and hydrogenated lanolin,
n is a number between 0.5 and 10, and
$R_1$ and $R_2$ are selected from the group consisting of lower alkyl containing 1-4 carbon atoms and lower hydroxyalkyl wherein the alkyl moiety contains 1-4 carbon atoms, or $R_1$ and $R_2$ together with the nitrogen atom to which they are attached form a heterocycle containing 5 or 6 chains, and
(2) a surfactant of the formula

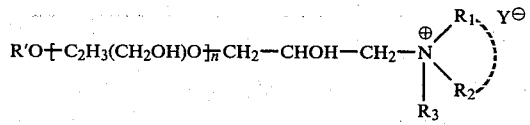

wherein
R' represents a hydrocarbon radical derived from a member selected from the group consisting of alcohols and sterols of a member selected from the group consisting of lanolin and hydrogenated lanolin,
n is a number between 0.5 and 10,
$R_1$ and $R_2$ are selected from the group consisting of lower alkyl containing 1-4 carbon atoms and lower hydroxyalkyl wherein the alkyl moiety contains 1-4 carbon atoms, or $R_1$ and $R_2$ together with the nitrogen atom to which they are attached form a heterocycle containing 5 or 6 chains,
$R_3$ represents lower alkyl having 1-2 carbon atoms, and
Y represents a member selected from the group consisting of Cl, Br, I, $CH_3SO_4$ and $C_2H_5SO_4$,
(b) from 5 to 60 percent by weight, as the oil phase a member selected from the group consisting of a fatty body, a synthetic oil, a mineral oil, an animal oil, a vegetable oil and a wax, and
(c) from 10 to 95 weight percent water.

* * * * *